(12) United States Patent
Baron et al.

(10) Patent No.: US 9,234,828 B2
(45) Date of Patent: Jan. 12, 2016

(54) FREE FLOATING TILT HYDROMETER

(71) Applicant: Baron Brew Equipment, Santa Rosa, CA (US)

(72) Inventors: Noah Ananda Baron, Santa Rosa, CA (US); Tyler Michelson Bryant, Santa Rosa, CA (US)

(*) Notice: Subject to any disclaimer, the term of this patent is extended or adjusted under 35 U.S.C. 154(b) by 334 days.

(21) Appl. No.: 13/843,515

(22) Filed: Mar. 15, 2013

(65) Prior Publication Data

US 2014/0260607 A1 Sep. 18, 2014

Related U.S. Application Data

(60) Provisional application No. 61/639,886, filed on Apr. 28, 2012.

(51) Int. Cl.
*G01N 9/00* (2006.01)
*G01N 9/12* (2006.01)
*G01N 9/16* (2006.01)
*G01N 9/18* (2006.01)

(52) U.S. Cl.
CPC .. *G01N 9/12* (2013.01); *G01N 9/16* (2013.01); *G01N 9/18* (2013.01)

(58) Field of Classification Search
CPC .................................. G01N 9/12; G01N 9/18
USPC .................................... 73/448, 305, 306, 319
See application file for complete search history.

(56) References Cited

U.S. PATENT DOCUMENTS

| | | | | |
|---|---|---|---|---|
| 5,655,403 A | * | 8/1997 | Topliff | G01D 5/34 33/759 |
| 6,422,746 B1 | * | 7/2002 | Weiss | B63B 22/18 116/204 |
| 2007/0028688 A1 | * | 2/2007 | Balogh | G01P 15/125 73/514.06 |
| 2007/0221233 A1 | * | 9/2007 | Kawano | A61B 1/00016 128/899 |
| 2009/0281686 A1 | * | 11/2009 | Smith | B63C 1/06 701/21 |
| 2011/0053283 A1 | * | 3/2011 | Hood | G01N 33/14 436/104 |

* cited by examiner

*Primary Examiner* — Hezron E Williams
*Assistant Examiner* — Tarun Sinha
(74) *Attorney, Agent, or Firm* — Jura C. Zibes; Gregory N. Brescia; Wilson, Elser, Moskowitz, Edelman & Dicker LLP

(57) ABSTRACT

A hydrometer embodied as self-contained buoyant structure that reacts to the buoyant force of a fluid by equilibrating at a tilt. The tilt of the structure can then be used to calculate the specific gravity of the fluid. In one embodiment, an accelerometer for measuring the inclination of the buoyant structure, a radio for transmitting the data wirelessly and a battery is contained within the buoyant structure, which allows for a convenient, and efficient automated process for monitoring the specific gravity of a liquid.

15 Claims, 5 Drawing Sheets

FREE FLOATING TILT HYDROMETER

CROSS-REFERENCE TO RELATED APPLICATIONS

Provisional Application No. 61/639,886, filed on Apr. 28, 2012

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

FIELD OF THE INVENTION

The present invention relates generally to an apparatus and method for determining the specific gravity of liquids in chemical, biological, or mechanical processes.

BACKGROUND OF THE INVENTION

A hydrometer is a common way of measuring the specific gravity of a liquid. The classic hydrometer is an instrument that typically finds its place on a lab bench. It is composed of glass and consists of a cylindrical stem, weighted with mercury or lead shot to make it float upright, and the upper stem is marked with a scale, so that the specific gravity can be read directly. The classic hydrometer is used by collecting a sample of liquid of unknown specific gravity, pouring it into a graduated cylinder or a similar container, the hydrometer is then placed to free float in the cylinder, and height of the water relative to the hydrometer is measured by the calibrated marks on the stem. The problem with the traditional hydrometer is that it cannot provide in situ measurements, it is fragile, it is time consuming to take measurements, and it does not provide electronic data.

Another type of hydrometer is the swing arm hydrometer. There are a series of swing arm hydrometers that are self-contained hand held instruments and others that measure in situ. The swing arm is a flotation device that rotates around a fixed axis in response to the buoyant force of the liquid being measured. The portable swing arm hydrometer simply consists of a box, a swing arm and a counter weight. The specific gravity of a sample liquid may be taken with the portable version on site but a sample must be removed, sampled and disposed of. The in situ type of swing arm hydrometer does not require the removal of a sample of liquid for testing. The problem with the swing arm hydrometer is that it is hard to install, hard to clean, and cumbersome to use.

Another type of hydrometer floats freely in a liquid to provide in situ specific gravity measurements. This hydrometer consists of a weighted float, a horizontal arm and a scale. The buoyant force of the liquid causes the hydrometer to float at varying vertical tilts. The change in tilt is measured by a combination of a mechanical arm that moves in relationship to the weighted float and a scale that reports the specific gravity. The problem with this hydrometer is that it requires a mechanical arm to be attached to the hydrometer.

BRIEF SUMMARY OF THE INVENTION

In accordance with the invention, the hydrometer is a self contained, free floating device that can either transmit or contain data relating to the float angle of the hydrometer as it relates to specific gravity. This device allows automated accurate real time measurements of the specific gravity of a liquid, in situ that can be transmitted wirelessly to a computer for evaluation or read off of the hydrometer without contaminating or disturbing the liquid being measured.

One embodiment of the invention automates and streamlines the process of obtaining specific gravity measurements by including an accelerometer, a radio and power source in a weighted free-floating, buoyant container. This allows for real time electronic measurements of the inclination of the float structure that may be received by a smart phone radio receiver or other means of receiving and displaying data. The data may be received by a computer which can then calculate the specific gravity based on the measurements generated by the accelerometer and transmitted to the computer or database by the radio within the container. An antenna boom may be added to increase the transmission distance.

In another embodiment of the invention, the free-floating, weighted hydrometer may include graduated markings on the float structure for determining the float angle visually. The graduated marks may be observed through various visual means including a video recorder, camera and or visually. In this embodiment, a power source or radio for transmitting data is not needed.

In another embodiment of the invention, the need for a radio transmitter and power source within the float devise may be eliminated by adding a magnetic bar such that an exterior magnetic reader may be used to determine the float angle from a scan of the independent hydrometer.

The invention provides accurate readings even in a turbulent liquid because the average value will provide accurate measurements. Electronic measurements and logging allow easily calculated averages. To provide more stable readings a fin may be attached to the hydrometer or the hydrometer may be stabilized by another hydrodynamic form.

In yet another embodiment, a temperature and pressure gauge may be added to the invention to correct for minor variations in specific gravity due to these variables.

BRIEF DESCRIPTION OF THE DRAWINGS

The subject matter, which is regarded as the invention, is particularly pointed out and distinctly claimed in the claims at the conclusion of the specification. The foregoing and other features and advantages of the invention will be apparent from the following detailed description taken in conjunction with the accompanying drawings in which:

DETAILED DESCRIPTION OF THE INVENTION

It should be understood that the embodiments detailed above are only some examples of the many possible forms that the invention can use. In general, statements made in the specification of the present application do not necessarily limit any of the claims of the invention. Moreover, some statements may apply to some inventive features but not to others. In general, unless indicated, singular statements may be in the plural and vice-versa with no loss of generality.

The present invention relates to a hydrometer to measure the specific gravity of a liquid. The hydrometer is commercially useful in many industries, specifically is can be used in the beer, wine and spirits industry. To produce any type of alcohol including beer, wine and spirits sugar must be converted to alcohol. This is called the fermentation process. This process is monitored by taking samples of the fermenting liquid, and measuring specific gravity of the sample. The measurement continues for several days or several weeks until the process is complete, meaning most or all of the sugar has been converted to alcohol. The constant specific gravity measurements are essential for monitoring this process. The methods for testing the specific gravity in this industry require a sample to be taken out of the fermentation vessel. They do not provide for real time, in situ, automated sampling and measuring of specific gravity. If they do provide for this, the type of measuring apparatus is not as accurate, stable, free-floating and portable.

The hydrometer described in the present invention is designed such that it can be used in situ to determine the inclination of the float structure, provide stable readings, prevent contamination of liquid, and automate the measuring and recording process. The specific gravity may be calculated by taking a collection of tilt measurements in at least one calibration solution of known specific gravity to create a table to convert from measured tilt to specific gravity. For example, calibration can be achieved by taking a measurement in distilled water as well as in a known volume of water with known mass of sugar.

The invention improves on the prior art in that it is a self-contained and free floating hydrometer that provides reliable specific gravity measurements; it does not need to be attached to the container in which it floats, it does not need to be attached to any exterior or interior structure or device for measuring or stability. Several embodiments provide for an automated approach to the measuring, gathering, and transmission of specific gravity data in situ, whereas other embodiments provide for visual or magnetic measurements.

Figure 1:
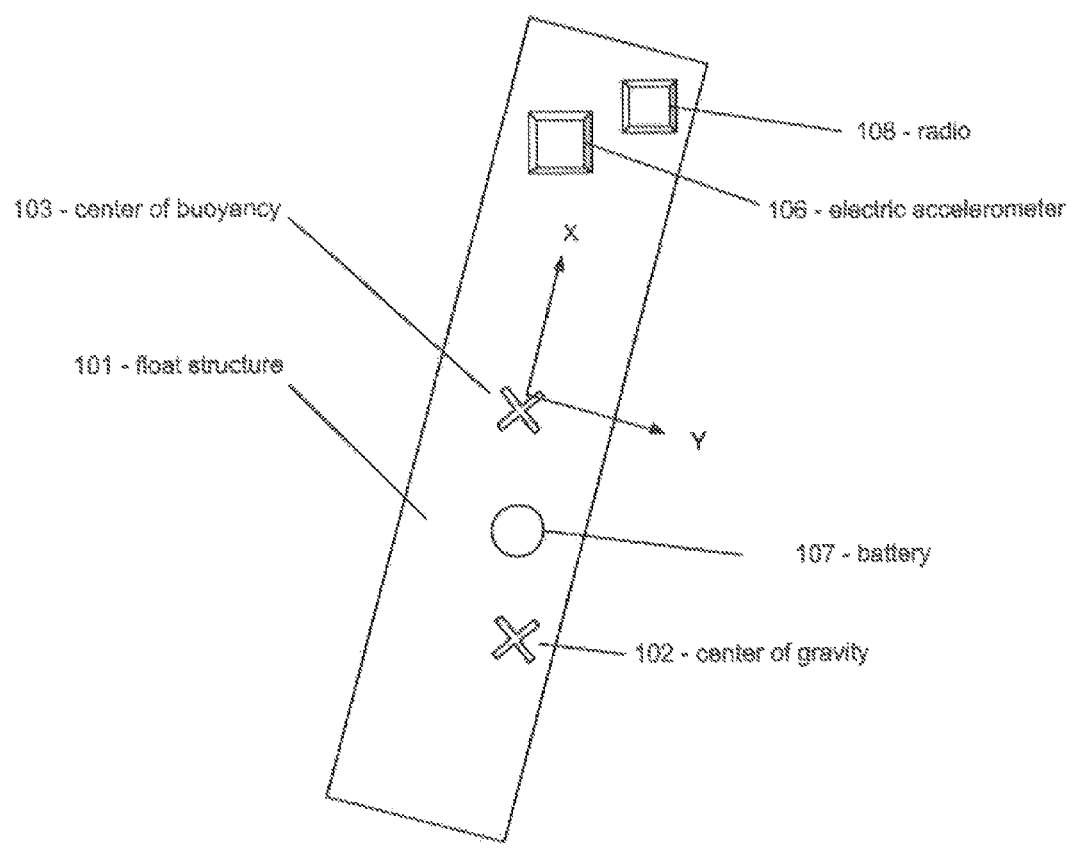
FIG. 1 illustrates a schematic representation of one embodiment of the present invention.

FIG. 1 depicts a view of an embodiment of the hydrometer. The float structure 101, which can be made of such materials as a hard plastic that is weighted such that there is a significant difference between the center of gravity 102 and the center of buoyancy 103 on the x and y axis of the float structure 101. The float structure 101 is also a waterproof container that encases an electronic accelerometer 106 as a measuring component, a battery 107 as a power source, and a radio 108 as a network-communicating module. This embodiment is capable of measuring real time specific gravity and to transmit the measurements over a network.

Figure 2:
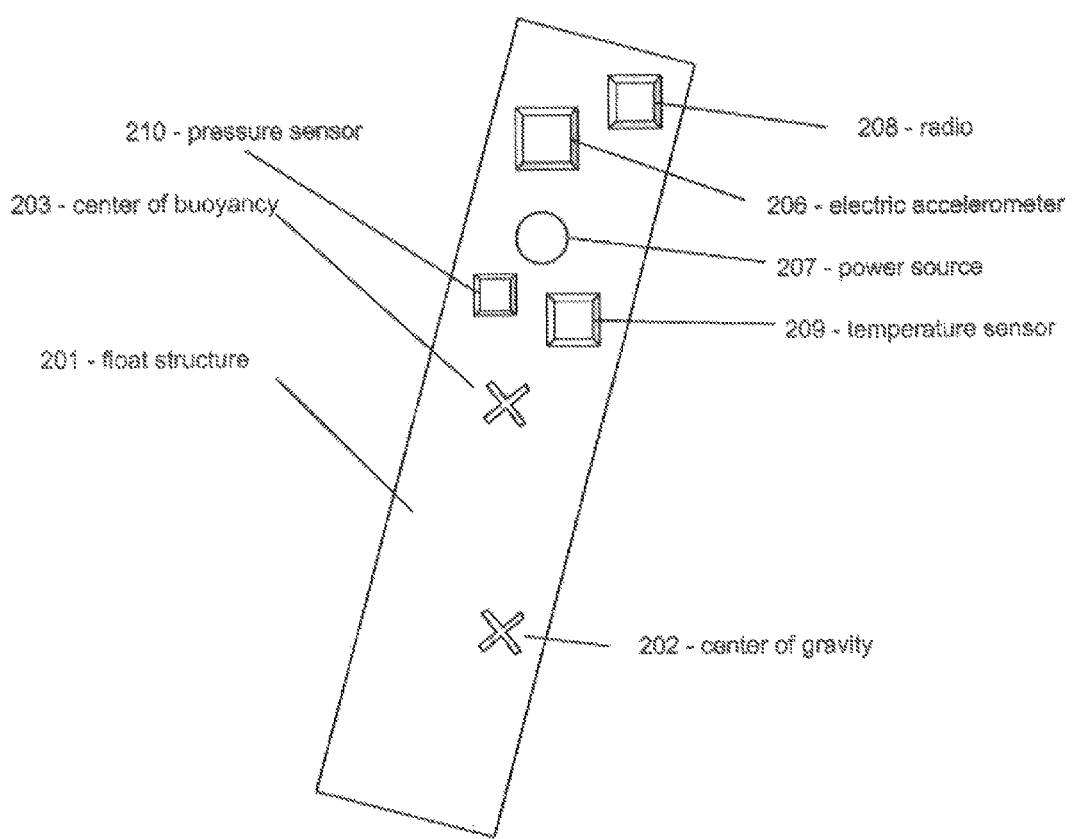
FIG. 2 illustrates a schematic representation of one embodiment of the present invention.

FIG. 2 depicts an embodiment includes the float structure or container 201, the center of gravity 202, the center of buoyancy 203, an electronic accelerometer 206, a power source 207 and a radio 208. This embodiment has the added benefit of a temperature sensor 209 and a pressure sensor 210. At least one useful purpose of these sensors is for adjusting slight specific gravity variations resulting from these variables.

Figure 3:
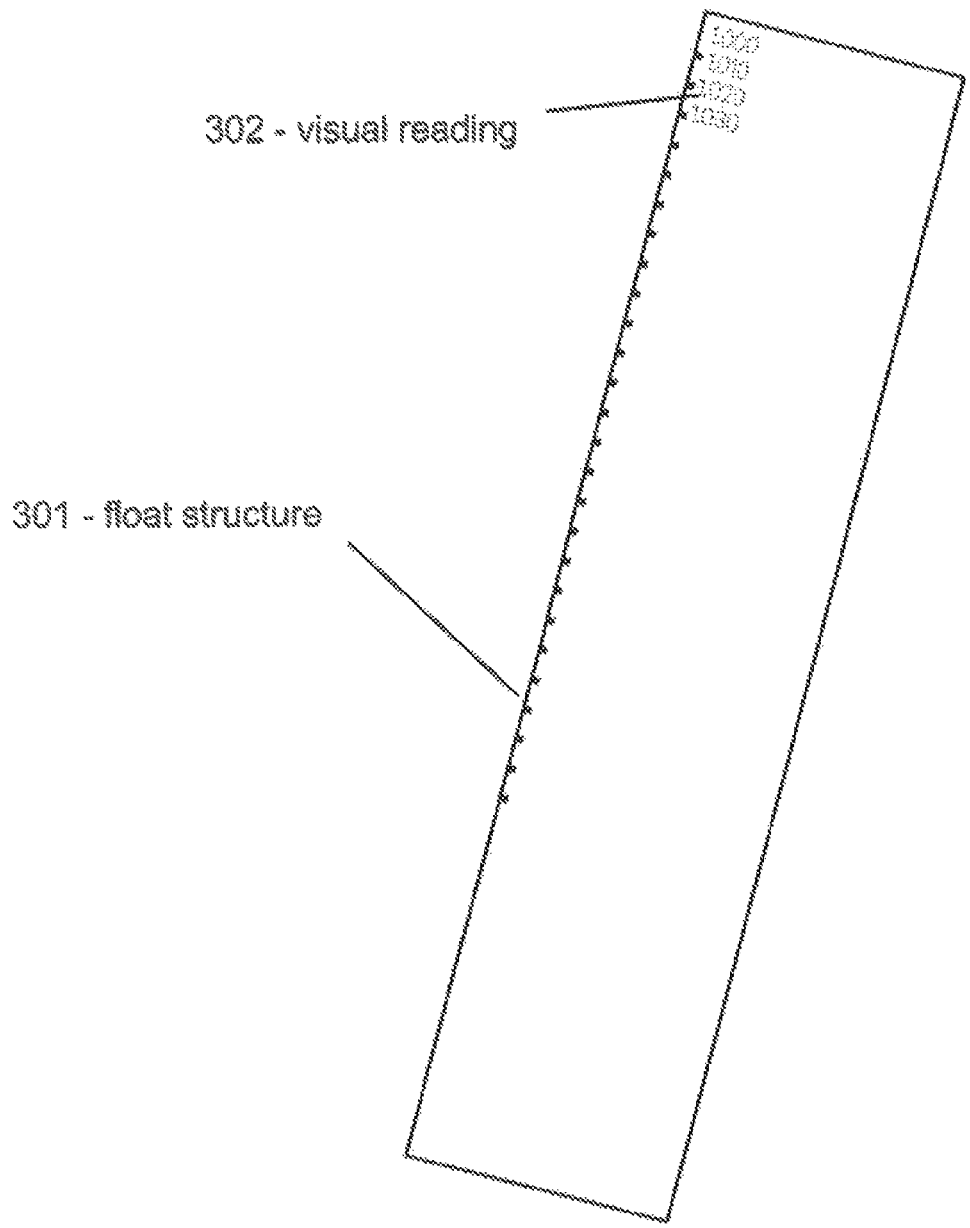
FIG. 3 illustrates a schematic representation of one embodiment of the present invention.

FIG. 3 depicts an embodiment that includes a float structure or container 301, which can made of such materials as a hard plastic. The float structure 301 has a center of mass and a center of buoyancy that are not coincident. The float structure 301 is marked strategically such that the specific gravity can be determined from a visual reading of the marks 302 in relationship to a liquid level of the fluid the structure 301 is floating in. The visual reading may be done by a person or by a camera, video recorder or some light capturing device.

Figure 4:
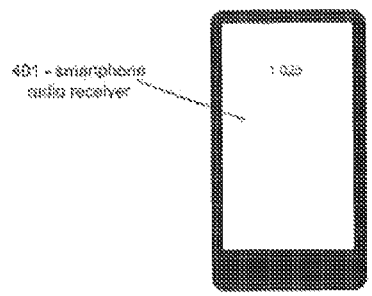
FIG. 4 illustrates a schematic representation of one embodiment of the present invention.

FIG. 4 depicts a smart phone radio receiver and display 401 as a means for capturing data from a network communicating device such as a radio contained in several embodiments above.

Figure 5:
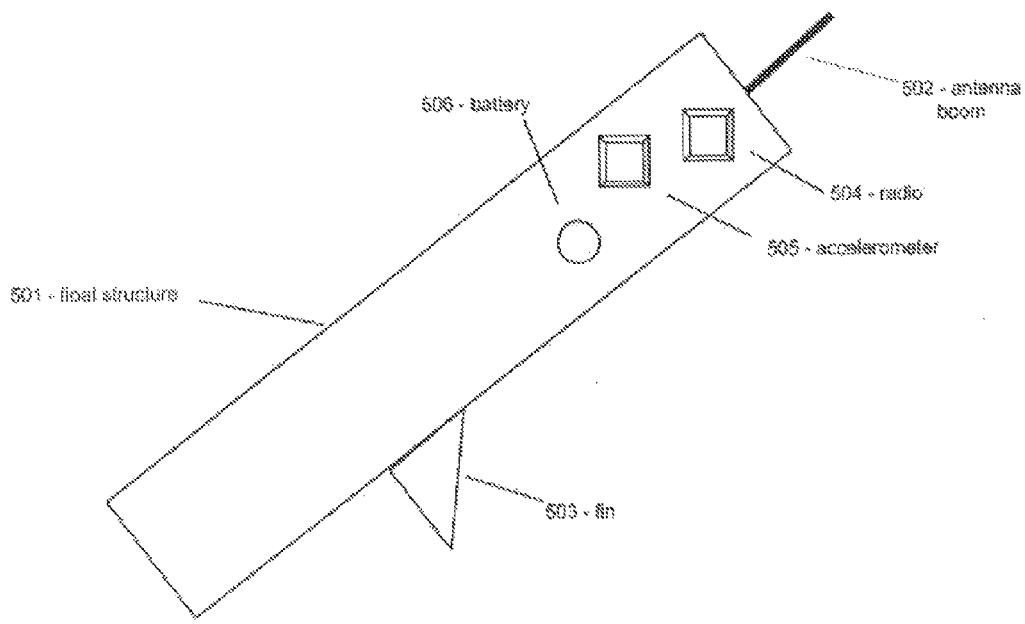
FIG. 5 illustrates a schematic representation of one embodiment of the present invention.

FIG. 5 depicts an embodiment that includes a float structure or container 501, which can made of such materials as a hard plastic. The float structure 501 has a center of mass and the center of buoyancy that are not coincident. The float structure is stabilized by one or more fins 503 such that it provides more accurate data. Any of the above embodiments, could benefit from the addition of a fin. A boom antenna 502 could be added to for increased transmission range of the radio 504 to transmit data from the accelerometer 505. The battery 506 is used to power the accelerometer 505 and radio 504.

Figure 6:
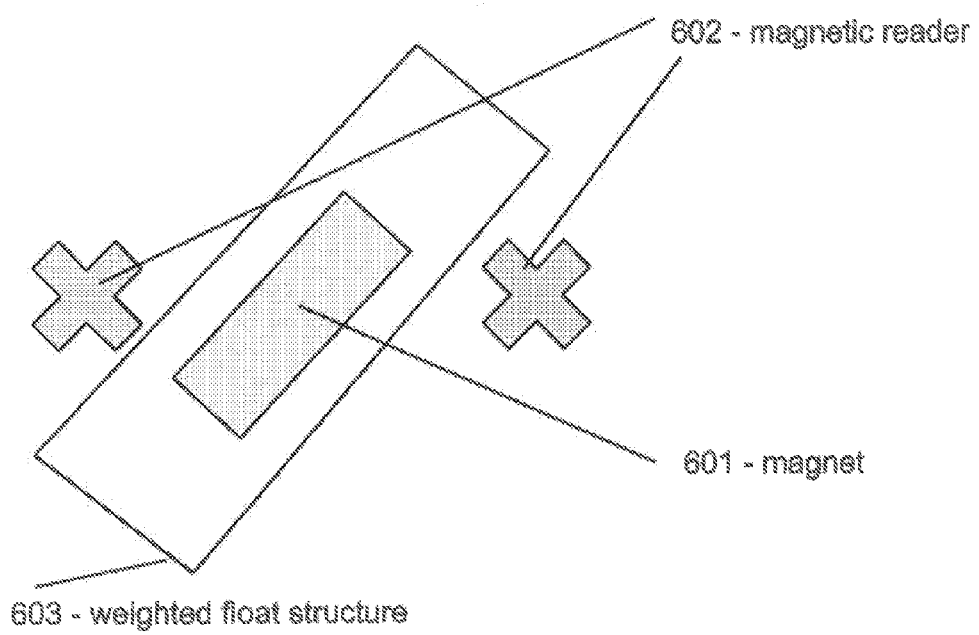
FIG. 6 illustrates a schematic representation of one embodiment of the present invention.

FIG. 6 depicts an embodiment that includes a weighted float structure 603 which could be a buoyant container where the center of mass and the center of buoyancy are not coincident which can be made of such materials as a hard plastic. The float structure further contains a magnet 601 useful for creating a magnetic field to be recorded by a magnetic reader 602, for determining the inclination of a float and calculating of the specific gravity.

It should be emphasized that the above-described embodiments of the invention is merely a possible example of implementations set forth for a clear understanding of the principles of the invention. Variations and modifications may be made to the above-described embodiment of the invention without departing from the spirit and principles of the invention. All such modifications and variations are intended to be included herein within the scope of the invention and protected by the following claims.

What is claimed is:

1. An apparatus comprising:
a float structure in which the center of mass and the center of buoyancy are not coincident;
a measuring component within or affixed to the float structure for measuring the inclination of the float structure indicating the specific gravity of a fluid;
a power source within or affixed to the float structure; and
a network communicating module within or affixed to the float structure for transmitting raw data.

2. The apparatus of claim 1, wherein the network communicating module send data to one or more external devices over a computer network.

3. The apparatus of claim 2, wherein the measuring component contains an accelerometer for determining the angle relative to gravity.

4. The apparatus of claim 3, wherein the float structure is optimized for increased stability.

5. The apparatus of claim 1, further comprising a temperature sensor for measuring the temperature of a fluid.

6. The apparatus of claim 1, further comprising a pressure sensor for determining the atmospheric pressure.

7. The apparatus of claim 1, further comprising of an antenna boom.

8. The apparatus of claim 1, further comprising a radio receiver and display.

9. The apparatus of claim 1, further comprising a component for calculating the specific gravity based on the measurements generated by the accelerometer and transmitted by the network communicating module.

10. The apparatus of claim 1, wherein the fermenting liquid is beer.

11. The apparatus of claim 1, wherein the fermenting liquid is wine.

12. The apparatus of claim 1, wherein the fermenting liquid is spirits.

13. A hydrometer comprising:
- a buoyant water-proof container, the container is weighted such that the center of buoyancy moves as the specific gravity of the fluid to be measured varies, and the resulting equilibrium tilt is an indication of the specific gravity of the fluid, the center of mass is also such that it is optimized to measure a particular range of specific gravity of a fluid;
- an accelerometer contained within the container for measuring the resulting equilibrium tilt;
- a battery contained within the container; and
- a radio contained within the float structure for transmitting raw data.

14. The apparatus of claim 13, wherein the radio sends data to one or more external devices over a computer network.

15. The apparatus of claim 13, further comprising a component for calculating the specific gravity based on the measurements generated by the accelerometer and transmitted by the radio.

\* \* \* \* \*